(12) United States Patent
Kimmel et al.

(10) Patent No.: US 10,970,655 B2
(45) Date of Patent: Apr. 6, 2021

(54) SURGERY PLANNING BASED ON PREDICTED RESULTS

(75) Inventors: Ron Kimmel, Haifa (IL); Michael Bronstein, Haifa (IL); Alexander Bronstein, Haifa (IL); Eitan Zeiler, Haifa (IL)

(73) Assignee: TECHNION RESEARCH & DEVELOPMENT FOUNDATION LTD, Haifa (IL)

( * ) Notice: Subject to any disclaimer, the term of this patent is extended or adjusted under 35 U.S.C. 154(b) by 2426 days.

(21) Appl. No.: 12/772,466

(22) Filed: May 3, 2010

(65) Prior Publication Data

US 2011/0270044 A1     Nov. 3, 2011

(51) Int. Cl.
*G16H 30/40*     (2018.01)
*A61B 34/10*     (2016.01)
(Continued)

(52) U.S. Cl.
CPC ........... *G06Q 10/06* (2013.01); *A61B 5/1077* (2013.01); *A61B 34/10* (2016.02); *G06F 19/00* (2013.01);
(Continued)

(58) Field of Classification Search
CPC .... A61B 5/1077; G06F 19/3437; G06Q 10/06
(Continued)

(56) References Cited

U.S. PATENT DOCUMENTS

| 5,325,293 A * | 6/1994 | Dorne ............................... 705/2 |
| 2004/0052409 A1 * | 3/2004 | Bansal et al. ................. 382/128 |

(Continued)

FOREIGN PATENT DOCUMENTS

| WO | WO 2005/067389 | 7/2005 |
| WO | WO 2007/069260 | 6/2007 |

OTHER PUBLICATIONS

Dragomir, A. et al., "SCAPE: Shape completion and animation of people", SIGGRAPH, vol. 24, Issue 3 (Jul. 2005).
(Continued)

*Primary Examiner* — Trang T Nguyen
(74) *Attorney, Agent, or Firm* — Trop, Pruner & Hu, P.C.

(57) ABSTRACT

A method for planning a current medical procedure to be performed on a body part of a current patient includes obtaining a current first representation of a surface of the body part of the current patient, and either obtaining a representation of a desired result surface for the current medical procedure or selecting parameters for the current medical procedure. The method further includes retrieving at least one best matching record from a database of records of previously performed medical procedures of previous patients, based on a similarity criterion. Each record includes: parameters of a previously performed procedure of the previously performed medical procedures, a first representation of the body part of the previous patient prior to performance of the previously performed procedure, and a second representation of a body part of the previous patient after the performance of the previously performed procedure. The method further includes determining parameters of the current medical procedure based on the parameters of the retrieved record, or generating a representation of a predicted result for the current medical procedure on the body part of the current patient based on the retrieved record.

13 Claims, 4 Drawing Sheets

(51) Int. Cl.
  *G06Q 10/06* (2012.01)
  *A61B 5/107* (2006.01)
  *G16H 50/50* (2018.01)
  *G06F 19/00* (2018.01)
  *G16H 70/20* (2018.01)
  *G06Q 10/10* (2012.01)

(52) U.S. Cl.
  CPC ............ *G16H 30/40* (2018.01); *G16H 50/50* (2018.01); *G16H 70/20* (2018.01); *A61B 2034/105* (2016.02); *G06Q 10/10* (2013.01)

(58) Field of Classification Search
  USPC .......................................... 705/2–3; 600/300
  See application file for complete search history.

(56) References Cited

U.S. PATENT DOCUMENTS

| | | | | |
|---|---|---|---|---|
| 2004/0146191 | A1* | 7/2004 | Lu | G06T 19/00 382/128 |
| 2004/0181430 | A1* | 9/2004 | Fotsch | G06F 19/3418 705/2 |
| 2008/0159608 | A1* | 7/2008 | Suetens | G06T 19/20 382/128 |
| 2008/0235052 | A1* | 9/2008 | Node-Langlois et al. | 705/3 |

OTHER PUBLICATIONS

Besl, P.J. and McKay, N.D., "A Method for Registration of 3-D Shapes", IEEE Trans. on Pattern Analysis and Machine Intelligence, vol. 14. No. 2, Feb. 1992.

Blanz, Volker and Vetter, T., "A Morphable Model for the Synthesis of 3D Faces, SIGGRAPH", 1999.

Bronstein, A.M. et al., "Generalized multidimensional scaling: a framework for isometry-invariant partial surface matching", *Proc. National Academy of Sciences*, 2006.

Yang, Chen and Medioni, G., "Object modeling by registration of multiple range images", Int. Conf. on Robotics and Automation, 1991. Image and Vision Computing vol. 10, Issue 3, Apr. 1992.

Elad, Asi, and Kimmel, Ron. "On bending invariant signatures for surfaces", *IEEE Trans. on Pattern Analysis and Machine Intelligence*, vol. 25, No. 10, Oct. 2003.

Memoli, Facundo and Sapiro, G.,"A theoretical and computational framework for isometry invariant recognition of point cloud data", *Found. Comput. Math.*, vol. 5, No. 3, Jul. 2005.

Weise, Thibaut et al., "Face/Off: live facial puppetry", Symposium on Computer Animation, 2009.

Kimmel, R and Sethian, J. A., "Computing geodesic paths on manifolds", *Proc. of National Academy of Sciences*, 1998.

* cited by examiner

SURGERY PLANNING BASED ON PREDICTED RESULTS

FIELD OF THE INVENTION

The present invention relates to surgery planning. More particularly, the present invention relates to a method and system for planning a surgical procedure based on predicted results.

BACKGROUND OF THE INVENTION

The predicted outcome of a medical operation is of concern to patients and surgeons. This may be especially true with regard to the fields of plastic, aesthetic, reconstructive, and cosmetic surgery. In these fields, a body part may be reshaped or modified in order to improve the appearance of the patient. In such a case, prediction and visualization of the results may play an important role in planning the surgery. For example, the predicted appearance of the patient after the procedure may be a major factor in planning, or in deciding whether or not to perform, a surgical procedure such as rhinoplasty or breast augmentation.

Typically, a physician and patient may attempt to visualize a likely outcome of a surgical procedure on the basis of photographs that show the results of past procedure. For example, a physician may maintain an album of photographs of patients before and after surgery. The physician may then attempt to select from the album photographs of patients whose pre-surgery appearance most closely resembles that of the present patient, and who underwent a surgical procedure closely resembling a proposed procedure. However, prediction based on such photographs may not be satisfactory. For example, differences among patients and among the details of surgical procedures may detract from the relevance of such comparisons and reduce the reliability of a prediction based solely on such photographs.

Computer imaging and image processing techniques may be utilized in predicting results a surgical procedure. Such techniques have been developed and described in the context of a number of different fields for application within a number of contexts, such as, for example, animation and forensics. Such techniques may include scanning or otherwise measuring the topography of a surface so as to acquire a digitized three dimensional representation of a surface. Various surface scanning methods have been described. For example, techniques have been described in which one or more cameras are used to acquire images of as surface. The images may then be analyzed to yield a three dimensional description of the surface. For example, triangulation techniques may be applied to images of a surface acquired from different viewing angles to produce a three dimensional characterization of the surface. Another technique known in the art uses detection of a pattern projected onto a contoured surface to generate a three dimensional description of the surface. A variation of this technique for rapidly acquiring a three dimensional description of a contoured surface has been described by Kimmel in WO 2005/067389.

Once a three dimensional description of a surface is acquired, various shape modification techniques may be applied to produce a predicted surface after surgery. For example, a shape modification technique may be applied to produce and display a modified surface whose shape has been deformed in a realistic manner from the original surface as a result of a particular defined process. Such deformation may be based on a theoretical model that describes deformation of a shape upon application of various deforming factors or forces. However, the accuracy of such predictive techniques may be limited by the accuracy of the theoretical model. In addition, a particular theoretical model may have limited applicability to a particular surgical procedure. It would therefore be advantageous to use an empirical model based on actual surgical results.

In building an empirical model, it is necessary to quantitatively describe a change in the shape of a surface as a result of application of a particular surgical procedure. A quantitative description of a displacement of each point of the pre-surgery surface to the position of a corresponding point of the post-surgery surface may be referred to as a deformation map. Since the correspondence between a point of the post-surgery surface and a point of the pre-surgery surface may not be known a priori, the correspondence may have to be calculated. Techniques have been developed for automatically constructing such a correspondence based on metric structure similarity. The main idea of such techniques is to find a correspondence between two surfaces that preserves point-wise distances (metric) on the surfaces. For example, Kimmel et al. in WO 2007/069260 describe a method based on finding minimum-distortion correspondence between two non-rigid surfaces, where the distortion reflects the metric dissimilarity of the two surfaces under a given correspondence. By minimizing the correspondence distortion, one obtains the best matching between the surfaces. The method described is based on calculating distances between pairs of points, on both surfaces being matched. These distances define the metric structure of each of the surfaces. Depending on the specific way of computing the distances, special invariance properties can be achieved. For example, geodesic distance, defined as the length of the shortest path on the surface connecting two points, does not change when the surface undergoes non-rigid deformations. Thus, geodesic metric structure of a surface is deformation invariant, which makes the correspondence based on minimization of geodesic metric dissimilarity be agnostic to shape deformations.

The computation of the minimum-distortion correspondence can be performed by an iterative procedure, as follows. The two surfaces are sampled at some fixed number of points, and the pair-wise distances between each pair of points in the set of points on each surfaces is computed. The correspondence between the two sets of points is initialized by some initial correspondence that may be selected at random or provided based on some side information. Given a correspondence, its distortion may be quantified based on a comparison of the distance between pairs of points on one surface and the corresponding pairs of points on another surface. The distortion can be quantified by, for example, the average absolute difference between corresponding distances or the maximum absolute difference between corresponding distances. The correspondence is then modified iteratively so that the value of the distortion is decreased. When the distortion falls below some threshold value or cannot be decreased by subsequent iterations, the procedure is terminated and the current correspondence is considered optimal. The modification of the correspondence during the iteration process may be performed by perturbation of the corresponding points and re-computation of the distances between them.

It is an object of the present invention to provide a system and method for reliably predicting the shape of the surface of a part of a patient's body as a result of a surgical procedure.

Other aims and advantages of the present invention will become apparent after reading the present invention and reviewing the accompanying drawings.

SUMMARY OF THE INVENTION

There is thus provided, in accordance with some embodiments of the present invention, a method for planning a current medical procedure to be performed on a body part of a current patient. The method includes:

obtaining a current first representation of a surface of the body part of the current patient;

obtaining a current second representation of a desired result surface for the current medical procedure;

retrieving at least one record from a database of records of previously performed medical procedures of previous patients, in which each record includes parameters of a previously performed procedure of the previously performed medical procedures, a first representation of the body part of the previous patient prior to performance of the previously performed procedure, and a second representation of a body part of the previous patient after the performance of the previously performed procedure, the retrieved record being a best matching record based on a similarity criterion;

determining parameters of the current medical procedure based on the parameters of a previously performed procedure of the retrieved record.

Furthermore, in accordance with some embodiments of the present invention, the step of obtaining a current first representation includes scanning the body part.

Furthermore, in accordance with some embodiments of the present invention, the step of obtaining a current second representation includes deforming the first representation.

Furthermore, in accordance with some embodiments of the present invention, the similarity criterion refers to a similarity selected from a list of similarities consisting of:

similarity between the current second representation and the second representation of a record of the database of records;

similarity between the current first representation and the first representation of a record of the database of records; and similarity between a deformation map representing transformation of the current first representation into the current second representation and a deformation map representing transformation of the first representation into the second representation of a record of the database of records.

Furthermore, in accordance with some embodiments of the present invention, the method includes billing a user per consultation.

There is further provided, in accordance with some embodiments of the present invention, a method for predicting a result of a current medical procedure to be performed on a body part of a current patient. The method includes:

obtaining a current first representation of a surface of the body part of the current patient;

selecting parameters for the current medical procedure;

retrieving at least one record from a database of records of previously performed medical procedures of previous patients, in which each record includes parameters of a previously performed procedure of the previously performed medical procedures, a first representation of the body part of the previous patient prior to performance of the previously performed procedure, and a second representation of a body part of the previous patient after the performance of the previously performed procedure, the retrieved record being a best matching record based on a similarity criterion; and generating a current second representation of a predicted result for the current medical procedure on the body part of the current patient, based on the retrieved record.

Furthermore, in accordance with some embodiments of the present invention, the step of obtaining a current first representation includes scanning the body part.

Furthermore, in accordance with some embodiments of the present invention, the similarity criterion refers to a similarity selected from a list of similarities consisting of:

similarity between the selected parameters and the parameters of a record of the database of records; and similarity between the current first representation and the first representation of a record of the database of records.

Furthermore, in accordance with some embodiments of the present invention, the step of generating a current second representation includes calculating a deformation map representing transformation of the first representation of the retrieved record into the second representation of the retrieved record and applying the calculated deformation map to the current first representation.

Furthermore, in accordance with some embodiments of the present invention, the method includes displaying the current second representation.

Furthermore, in accordance with some embodiments of the present invention, the method includes billing a user per consultation.

There is further provided, in accordance with some embodiments of the present invention, a system for planning a current medical procedure to be performed on a body part of a current patient. The system includes:

at least one input device for inputting a current first representation of a surface of the body part of the current patient and for inputting an input data selected from a list of input data consisting of: a current second representation of a desired result surface for the current medical procedure and selected parameters for the current medical procedure;

a storage device for storing a database of records of previously performed medical procedures of previous patients, in which each record includes parameters of a previously performed procedure of the previously performed medical procedures, a first representation of a body part of the previous patient prior to performance of the previously performed procedure, and a second representation of the body part of the previous patient after the performance of the previously performed procedure; and a processing unit for retrieving at least one best matching record of the database based on similarity criterion and for returning an output data based on the best matching record and corresponding to content of the input data.

Furthermore, in accordance with some embodiments of the present invention, the output data is selected from a list of output data consisting of: parameters of the current medical procedure, and a representation of a predicted result for the current medical procedure when performed in accordance with the selected parameters.

Furthermore, in accordance with some embodiments of the present invention, the representation of a predicted result includes a deformation map.

Furthermore, in accordance with some embodiments of the present invention, the processing unit is connectable to the input device via a network.

Furthermore, in accordance with some embodiments of the present invention, the processing unit is connectable to the storage device via a network.

Furthermore, in accordance with some embodiments of the present invention, the system includes a scanner.

There is further provided, in accordance with some embodiments of the present invention, a computer program product stored on a non-transitory tangible computer readable storage medium for planning a current medical procedure to be performed on a body part of a current patient. The computer program includes code for:

obtaining a current first representation of a surface of the body part of the current patient;

obtaining a current second representation of a desired result surface for the current medical procedure;

selecting parameters for the current medical procedure;

retrieving at least one record from a database of records of previously performed medical procedures of previous patients, in which each record includes parameters of a previously performed procedure of the previously performed medical procedures, a first representation of the body part of the previous patient prior to performance of the previously performed procedure, and a second representation of a body part of the previous patient after the performance of the previously performed procedure, the retrieved record being a best matching record based on a similarity criterion;

determining the parameters of the current medical procedure based on the parameters of the retrieved record;

generating a current second representation of a predicted result for the current medical procedure on the body part of the current patient, based on the retrieved record.

Furthermore, in accordance with some embodiments of the present invention, the computer code for obtaining a current first representation includes code for obtaining data from a scanner.

Furthermore, in accordance with some embodiments of the present invention, the computer code for generating a current second representation includes code for calculating a deformation map based on the first representation and the second representation of the retrieved record and applying the deformation map to the current first representation.

Furthermore, in accordance with some embodiments of the present invention, the similarity criterion refers to a similarity selected from a list of similarities consisting of:

similarity between the current second representation and the second representation of a record of the database of records;

similarity between the current first representation and the first representation of a record of the database of records;

similarity between a deformation map of a transformation of the current first representation into the current second representation and a deformation map of a transformation of the first representation into the second representation of a record of the database of records; and similarity between the selected parameters and the parameters of a record of the database of records.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Embodiments of the invention may include an article such as a computer or processor readable medium, or a non-transitory tangible computer readable storage medium such as, for example, a memory, a disk drive, or a USB flash memory, encoding, including or storing instructions, e.g., computer-executable instructions, which when executed by a processor or controller, carry out methods disclosed herein.

Surgery result visualization in accordance with embodiments of the present invention includes providing a database of results of previously performed surgical procedures, acquiring a current representation of the surface of a body part of a current patient on which a surgical procedure is proposed, retrieving an appropriate procedure result from the database based on similarity criteria, and applying the selected result to the acquired surface representation to create a predicted result of the proposed surgical procedure. The predicted result may be displayed as an image that may be viewed by a patient or by a physician.

In some embodiments of the present invention, a result of a proposed surgical procedure may be predicted on the basis of a current surface representation representing a current body part on which the procedure is to be performed, and a database of records of previously performed procedures. For example, each record of the database may include a pre-procedure surface representation of a similar body part of another patient before performance of a previous procedure, and a post-procedure representation of the body part after performance of the previous procedure. A predicted shape of the current body part as the result of the proposed procedure may computed as follows: A correspondence may be found between the current surface representation and a pre-procedure surface representation in a record of the database, for example, by minimizing metric distortion. Distortion is understood as quantifying some structural dissimilarity between two surface representations. The distortion computed in the minimization process may serve as a criterion of similarity of two surfaces. In this manner, a matching record of a previous procedure in which the pre-procedure body part most closely resembles the current body part may be selected.

Once a record is selected, a deformation map representing the transformation of the pre-procedure shape into the post-procedure shape may be computed. Deformation is understood as referring to a change applied to one surface to make the shape of the surface similar to the shape of a second surface. Alternatively, such a transformation can be pre-computed in advance and stored as part of the record.

Using a correspondence between the current representation and the pre-procedure representation of a matching record, the deformation map of the record may be applied to the current representation. Applying the deformation map to the current representation may approximately represent a predicted result of the proposed procedure on the represented body part.

Each record of a database of previously performed surgical procedures, in accordance with embodiments of the present invention, typically includes: a set of parameters that characterize a surgical procedure; a pre-surgery representation of the surface of a body part on which the surgical procedure was performed; and a post-surgery representation of the surface of the body part after surgery was performed, a deformation map that describes the change in the surface of the body part as a result of the surgical procedure, or both.

Parameters that characterize a surgical procedure may include such parameters as, for example: the type of surgical procedure; size, model, material, shape, and any other relevant characteristics of an implant; implantation location and orientation of the implant; identity of the surgeon; location, characterization, and dimensions of tissue to be removed; characteristics of the body part other than size and shape; age, sex, height, and weight of the patient; medications administered in association with the procedure; or any other information that may be used to parameterize a surgical procedure.

A representation of a surface typically includes a set of point or facet coordinates that completely describes the surface at a required level of resolution. The required resolution may vary depending on the identity of the body part and the nature of the procedure. For example, the resolution required for breast enlargement or reduction surgery may be a few millimeters, while surgery on the face may require sub-millimeter resolution. Such a representation may be acquired using a three dimensional surface characterization technique as is known in the art. For example, a surface may be imaged using from several directions and a technique such as triangulation may be applied to the acquired images. Alternatively, any other technique known in the art for measuring a surface, including, for example, optical, mechanical, acoustic, or electromagnetic devices, may be used to acquire a surface representation. Typically, a technique involving a light source and image acquisition device, such as the technique described by Kimmel in WO 2005/067389, may be used.

In addition, or alternatively to, a full three dimensional representation of the surface, the surface may be characterized by a set of parameters. For example, a surface may be represented by a limited set of predefined dimensions, curvatures or geometric moments. The number and nature of the surface parameters may depend on the type of body part whose surface is being described. For example, the parameters required to describe the shape of a breast may differ from those required to identity the shape of a nose or ear. A parametric representation may be derived from a full three dimensional representation of the surface. Such a parametric representation of the surface may be useful when searching the database for a surface representation that matches another given representation.

A deformation map is typically derived from a representation of a pre-surgery surface of a body part prior to performing a surgical procedure, and a representation of a post-surgery surface of the body part after the surgical procedure. Typically, a pair of pre-surgery and post-surgery surfaces, or a set of similar surfaces subject to a similar procedure, is analyzed to create a deformation map. The deformation map describes a change in the surface shape as a result of the surgical procedure. For example, the deformation map can be computed by first finding a minimum-distortion non-rigid correspondence as described by Kimmel et al. in WO 2007/069260 and then computing the displacement of the corresponding points. For example, the calculation may be based on metric structure similarity between the two surfaces, such as minimizing distortion of corresponding metric structures, such as geodesic distances, between the two surfaces. Alternatively, known techniques related to morphing may be utilized. Each set of parameters describing a surgical procedure and pre-surgery surface may thus be associated with a deformation map.

A surgery result visualization system, in accordance with embodiments of the present invention, may include one or more stations and a server communicating via a network. A station may include an input/output device for entering a surface representation and procedure parameters, and for receiving a data that describe the predicted results or for constructing a predicted result. A station also typically includes a display device, such as a monitor, for displaying the predicted results, and a device for acquiring a representation of a surface. The database, typically associated with a server, may cooperate with a network in order to enable access from a remote station or stations. Depending on the nature and relative locations of the stations and server, the network may be in the form of, for example, a direct connection, an intranet, or the Internet. Communication with the database may be performed via the server. The network connection may be utilized for entering data to add to the database, for managing data in the database, and for querying, and for communication between a station and the server.

Each station communicating with the surgery result visualization system may communicate separately with the system. For example, each station may be associated with a subscriber to the system. For example, a subscriber may be allowed free access to the system in exchange for a periodic fee. Alternatively, a user operating a station may be billed or charged per use (e.g. a pay-per-click model or pay per consultation model).

A surgery result visualization system in accordance with embodiments of the present invention may be used to plan a surgical procedure on a body part of a patient. The pre-surgery surface of the body part is scanned or otherwise measured, typically at a remote station, so as to create a pre-surgery representation of the surface. The pre-surgery representation may be analyzed to create a parametric representation of the pre-surgery surface.

A particular surgical procedure, described by characterizing parameters, may be proposed. Data, including the characterizing parameters and a representation of the current surface, may be input via a station and sent via the network to the server. The server may query the database to find a record of the database with data that form a best match to the input data. The query may return records of one or more previously performed procedures that match the input data.

In searching the database, a match between a record of a previously performed procedure in the database and input data that describes a proposed procedure may be determined on the basis of similarity criteria. For example, a match may not be required to be exact, but may require a degree of similarity based on a predetermined range. For example, a best match may be determined by maximizing a score based on a similarity between parameters of a procedure in the database and the input. For example, in calculating the score, parameters may be assigned weights that reflect their importance in finding a match. For example, in searching for a match to a proposed breast enlargement surgery, a search algorithm may be programmed to assign a greater weight to the size and location of the implant than to the identity of the surgeon. Criteria for determining a match typically include matching a pre-surgery surface associated with a previous procedure in the database with the input pre-surgery surface of the current patient. For example, a search may identify several records in which the parameters of the surgical procedure match those of the input data. From among those identified records, one or more records may be selected whose associated pre-surgery surfaces are sufficiently similar to the pre-surgery surface of the input data.

When one or more records of matching surgical procedures are selected from the database, a deformation map based on the selected records may be calculated. Typically, a deformation map is calculated from the pre-surgery and post-surgery surfaces of the selected records.

Alternatively, a pre-calculated deformation map may be retrieved from each record. Where appropriate, a deformation map may be calculated by interpolation or averaging between deformation map retrieved from several similar procedures. For example, the database search may retrieve records of two or more procedures that are similar to, but not identical to, the procedure of the input data. For example, the size of an implant to be implanted as part of the proposed procedure may lie between the sizes of the implants in two of the retrieved procedures. In such a case, it may be appropriate to calculate a deformation map for the proposed procedure by interpolating between, or averaging, deformation maps associated with the retrieved procedures.

Once a deformation map is obtained by calculation or retrieval, the deformation map may be applied to the representation of the input current surface. For example, a deformation map may include a set of vector displacements associated with points or facets of the pre-surgery surface representation. Application of the deformation map to the current representation then applies the vector displacement to each point or facet of the input surface representation. The result of application of the deformation map to the input surface is a representation of a predicted surface. Typically, application of the deformation map to the input surface is performed by the server. The representation of the predicted surface may then be sent via the network back to the remote station. At the remote station, the representation of the predicted surface may be rendered as an image and displayed on a display device, such as a monitor, associated with the remote station. Thus, the patient or the surgeon may review the displayed image of the predicted surface to see whether the predicted results are satisfactory. If not, the surgeon may propose an alternative proposed procedure and repeat the process.

Alternatively, the server may calculate or retrieve a deformation map and send the deformation map via the network to the remote station. A processor associated with the remote station may then apply the deformation map to the input representation of the current surface.

Alternatively or in addition, a user interface may be provided in which a user, such as a patient or surgeon, may manipulate a representation of a current surface. For example, the user interface may include image distortion and surface manipulation software tools as are known in the art. For example, a user may manipulate the surface to achieve a desired final, post-surgery, shape of the surface. An algorithm associated with the user interface may compute a desired deformation map that represents the change from the original shape to the desired shape. The desired deformation map may then be sent via the network to the server. The server may then query the database using the desired deformation map and a representation of the pre-surgery current surface as input. For example, each record may include a pre-calculated deformation map. For the purpose of expediting a search of the database for a matching pre-calculated deformation map, each pre-calculated deformation map may be parameterized. For example, a deformation map may be parameterized as the parameters of an appropriate set of parameterized three dimensional functions. The desired deformation map may then be input as a query to the database, together with a representation of current surface. The query to the database may return a record with a pre-calculated deformation map (and pre-surgery surface) that matches the input desired deformation map (and current surface). The parameters of a surgical procedure associated with the retrieved record may then define a surgical procedure that may be applied to the patient to achieve the desired result.

Reference is now made to the accompanying Figures.

Figure 1:
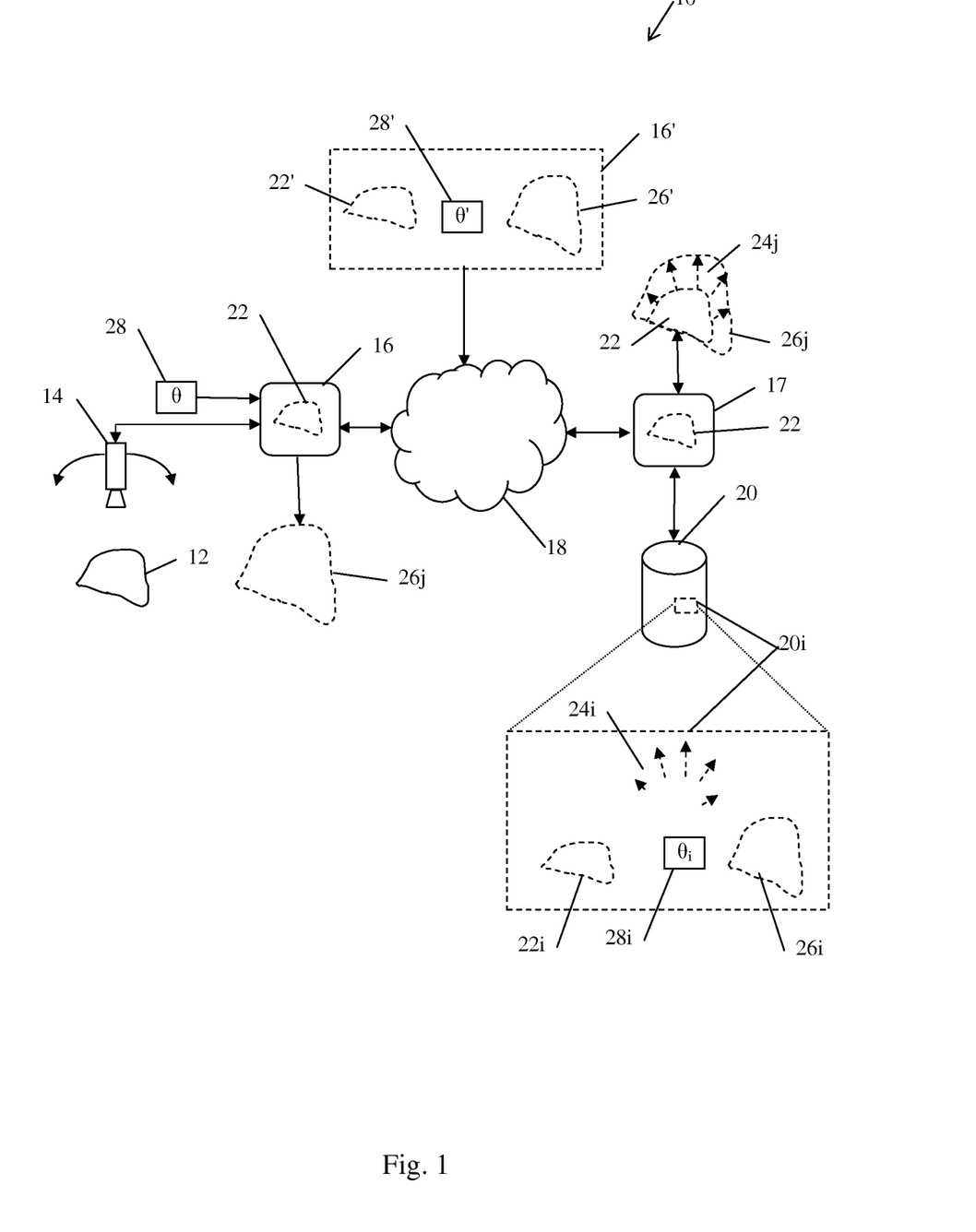
FIG. 1 schematically shows a system for visualizing predicted results of a surgical procedure in accordance with embodiments of the present invention.

FIG. 1 schematically shows a system for visualizing predicted results of a surgical procedure in accordance with embodiments of the present invention. Visualization system 10 typically includes a local station 16 connected via network 18 to database 20. Visualization system 10 may typically include other remote stations, such as remote station 16', each of which may communicate with database 20 via network 18.

Local station 16 may include one or more subsystems that communicate with one another so as to provide the function of local station 16. Typically, local station 16 may include or communicate with one or more computers, a display device such as a monitor, a user interface, and a scanning device 14. For example, local station 16 may control and receive scan data from scanning device 14. Scanning device 14 includes one or more component devices that may be used to acquire data that describes a scanned surface 12. For example, scanned surface 12 may represent the surface of a body part of a patient. For example, scanning device 14 may acquire surface data using any optical, acoustical, mechanical, electromagnetic, surface measurement device and method known in the art for measuring the shape of a surface. For example, scanning device 14 may include one or more cameras and cooperating light sources that may be scanned over scanned surface 12. Acquired data may be analyzed by one or more components of local station 16 to produce a surface representation 22 of scanned surface 12.

Surface representation 22 may be sent to server 17 via network 18. Network 18 may include any means of communication between local station 16 and server 17. For example, local station 16 and server 17 may be in the form of separate software modules of a single computer. In this case, network 18 represents communication between the modules via a computer program. Typically, local station 16 and server 17 reside on separate computers. In this case, network 18 represents communication between the separate computers via a wired or wireless connection, or via an external connection such as an intranet, the Internet, or any other communications channel between computers as is known in the art.

Server 17 typically communicates with database 20. Server 17 may represent a single computer, or may represent one or more components that cooperate to provide the function of server 17. Server 17 may manage and query database 20. Database 20 typically resides on one or more data storage units associated with server 17. Server 17 may input data to database 20, either as data to be added to the database, or as part of a query. For example, remote station 16' is shown communicating data to be added to database 20 via network 18. Typically, data communicated to database 20 may include a pre-surgery surface representation 22', a post-surgery surface representation 26', and a set of procedure parameters 28'. Typically, pre-surgery surface representation 22' may be acquired by a scanning device associated with remote station 16', by scanning the surface of a body part prior to performing a surgical procedure. Pre-surgery surface representation 22' may be in the form of, for example, a set of three dimensional coordinates of points of the represented surface, a set of values describing facets that represent the represented surface (e.g. facet coordinates and orientations, or of facet boundary definitions), or a set of parameters that describe the represented surface (e.g. dimensions and curvatures). Procedure parameters 28' may include parameters that describe the surgical procedure performed on the represented surface. For example, procedure parameters 28' may define aspects of the surgical procedure itself, the characteristics of the body surface (other than its shape), and any other information relevant to comparing one surgical procedure with another. Post-surgery surface representation 26' is typically acquired by the scanning device associated with remote station 16' by scanning the surface after performing the surgical procedure. Pre-surgery surface representation 22', post-surgery surface representation 26', and procedure parameters 28' may be transmitted by remote station 16' to server 17 via network 18. Server 17 may cause the transmitted data to be added as a record to database 20. Database 20 typically contains one or more stored and indexed records 20i. Typically, a record 20i includes a set of data that may include a pre-surgery surface representation 22i, an associated post-surgery surface representation 26i, and procedure parameters 28i. Records 20i of database 20 may be stored in a one or more storage media located at a single site, or in a distributed manner at two or more separate facilities linked via network 18.

Under predetermined conditions, a processor of server 17 may perform an analysis of one or more records 20i of database 20. Such predetermined conditions may include querying database 20 for records with data that match a set of input data, the addition of a predetermined number of records 20i to database 20, or predetermined times or time intervals. Typically, prior to performing an analysis, server 17 may retrieve from database 20 one or more records 20i that fit a set of input query data or other search criteria. Analysis may include calculating a deformation map 24i from one or more retrieved records 20i. Deformation map 24i may describe a transformation of a pre-surgery surface representation 22i to a post-surgery surface representation 26i when subject to a surgical procedure parameterized by procedure parameters 28i. A calculated deformation map 24i may be used immediately by server 17 to perform a calculation. Alternatively, a calculated deformation map 24i may be saved as part of record 20i, being indexed by associated procedure parameters 28i, by pre-surgery surface representation 22i, and optionally by post-surgery surface representation 26i.

Server 17 may utilize database 20 to predict the results of a surgical procedure on a surface 12. For example, surface 12 may be the surface of a body part of a patient considering undergoing a plastic surgery procedure. Surface 12 may be scanned by scanning device 14 associated with local station 16. Local station 16 may create surface representation 22 of surface 12 from the scan data. Surface representation 22 may include a full three dimensional representation of surface 12, for example, in the form of defined points or facets. Alternatively or in addition, surface representation 22 may include a parametric characterization of surface 12. Procedure parameters 28 defining a proposed surgical procedure may be input to local station 16 using a suitable user interface associated with local station 16.

Procedure parameters 28, surface representation 22, or both, may be transmitted to server 17 via network 18. Server 17 may use procedure parameters 28 and surface representation 22 to query database 20 for a matching record. For example, the query may entail searching database 20 for a record 20i with procedure parameters 28i that match input procedure parameters 28. One or more records of database 20 may be retrieved whose procedure parameters 28i sufficiently match the input procedure parameters 28 in accordance with search criteria. Match criteria may include ranking or weighting the importance of individual parameters of procedure parameters 28 in determining a match. Thus, equal values of one parameter may be considered more important than equal values of another parameter in determining a match. The query may in addition, or alternatively, entail searching database 20 for a record 20i with a pre-surgery surface representation 22i that matches input pre-surgery surface representation 22. For example, a query may return several records 20i of database 20 with procedure parameters 28i that match input procedure parameters 28. A subset of the returned records 20i may then be selected on the basis of a match between pre-surgery surface representation 22i of a record 20i and input pre-surgery surface representation 22.

Once one or more records 20i of database 20 are selected, server 17 may calculate a deformation map 24j. For example, server 17 may calculate deformation map 24j from one or more retrieved pre-surgery surface representations 22i and one or more retrieved post-surgery surface representations 26i. Alternatively, deformation map 24j may be calculated from one or more retrieved deformation maps 24i. For example, deformation map 24j may be calculated as an (possibly weighted) average of one or more retrieved deformation maps 24i.

Server 17 may apply deformation map 24i to pre-surgery surface representation 22. For example, deformation map 24j may include a set of vectors representing a set of translational or rotational displacements. For example, each displacement of deformation map 24j may be applied to a different part of pre-surgery surface representation 22 in order to produce a predicted post-surgery surface representation 26j. Alternatively, deformation map 24j may include a set of functions of any other form that may be applied to define the distortion of a surface. For example, deformation map 24j may be represented using coefficients in a polynomial, Gaussian, or spline function. Alternatively, deformation map 24j may be represented by a set of representative surface points for which deformation vectors are specified, with interpolation applied to describe distortion of other points of the surface.

Predicted post-surgery surface representation 26j may be transmitted back to local station 16, or any other remote station, via network 18. Alternatively, server 17 may transmit deformation map 24j to local station 16 via network 18. A processor of local station 16 may then apply deformation map 24j to pre-surgery surface representation 22 to create predicted post-surgery surface representation 26j.

A processor of local station 16 may render post-surgery surface representation 26j for imaging using an image rendering technique known in the art to produce a displayable image of the predicted post-surgery surface. The rendered image may be displayed on a screen or monitor of, or printed by a printer of, or otherwise displayed by, local station 16. The displayed image may be shown to a patient, surgeon, or other interested party, for approval. If approved, a surgeon may be instructed to perform the surgical procedure parameterized by procedure parameters 28. Otherwise, a surgeon may suggest an alternative procedure and the parameters of the alternative procedure may be input to local station 16 to be sent to server 17.

Figure 2:
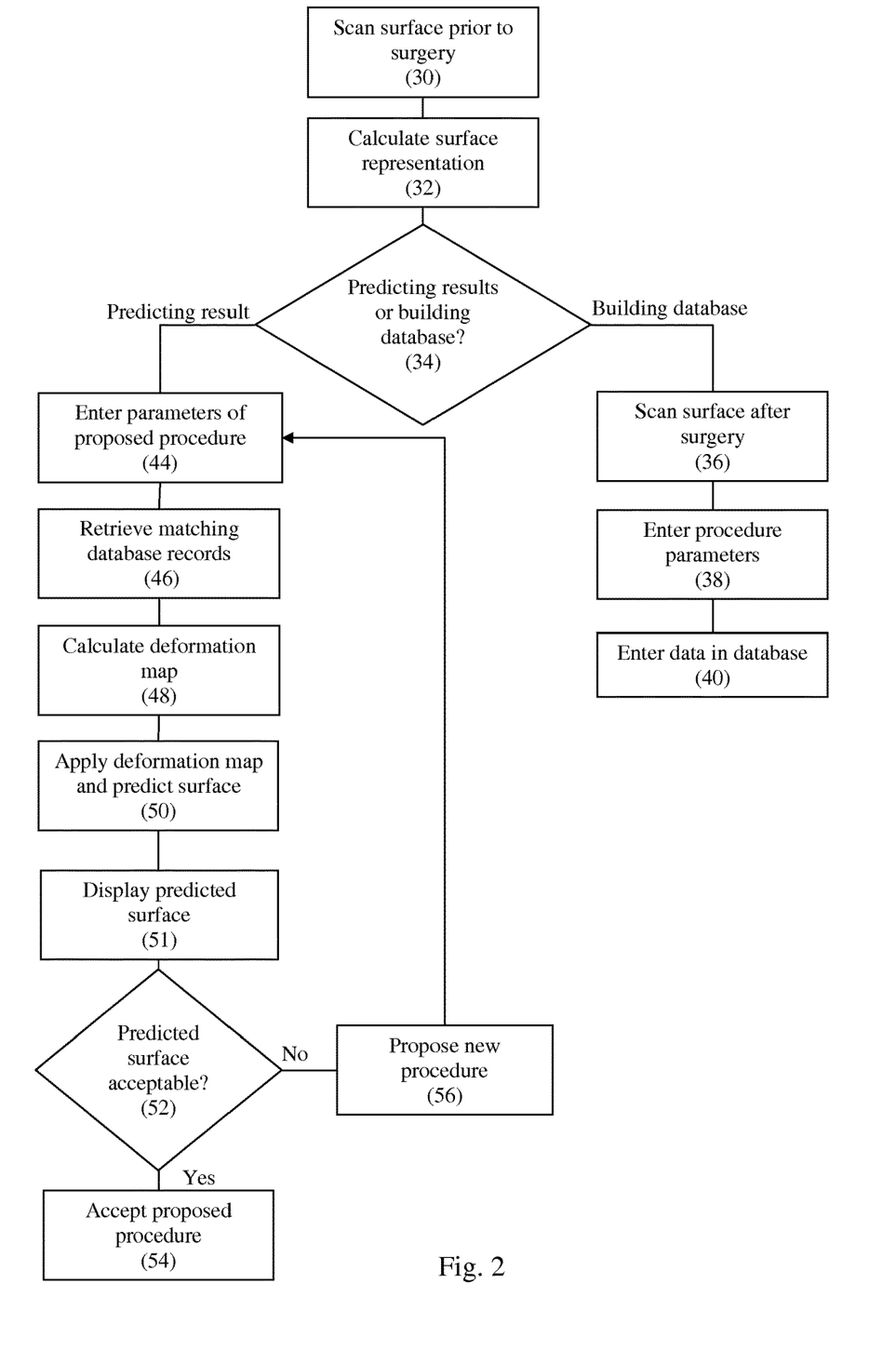
FIG. 2 is a flowchart of a method for visualizing predicted results of a surgical procedure in accordance with embodiments of the present invention.

FIG. 2 is a flowchart of a method for visualizing predicted results of a surgical procedure in accordance with embodiments of the present invention. Reference is also made to components of the system shown in FIG. 1. It should be understood that steps of the method are shown in a particular order for illustrative purposes only. It will be evident to one familiar with the art that in some cases, steps of the method may be performed in a different order, or concurrently, with equivalent effect. In addition, the grouping of activities associated with the method into separate steps is also selected for convenience and clarity of the presentation. In some cases, the activities may be grouped into an alternative set of discrete steps. All such alternative ordering or grouping should be considered as falling within the scope of the present invention.

A surface prior to surgery may be scanned by a scanning device associated with a local station 16 or remote station 16' (step 30). A processor typically associated either with the scanning device or with the local station converts the results of the scan to a surface representation 22 or 22' (step 32). The surface may be scanned either to provide data for indexed storage in database 20, or as part of a procedure to predict the results of a surgical procedure being planned (step 34).

When providing data for database 20, after the surgical procedure is performed, the surface as modified by the procedure is scanned again and the scan data converted to a surface representation such as post-surgery surface representation 26' (step 36). Parameters describing the surgical procedure performed are also entered (step 38). The scan representations and procedure parameters are entered as an indexed record into database 20 (step 40), for example, by a server 17.

When the surface is scanned as part of procedure to predict the results of a surgical procedure, a particular surgical procedure may be proposed. Parameters describing the proposed procedure may be entered or selected using a suitable input interface (step 44). The procedure parameters and, optionally, the surface representation may be input to database 20, typically via network 18 and server 17, as part of a query. Database 20 is then searched to locate one or more records that match the input data of the query in accordance with similarity or match criteria (step 46). A deformation map may be calculated from pre-surgery and post-surgery surface representations of the retrieved records, or from stored pre-calculated deformation maps (step 48). The calculated deformation map may then be applied to the scanned pre-surgery surface representation to yield a predicted post-surgery surface representation (step 50). The predicted post-surgery surface representation may be rendered as an image and shown to the patient or other party involved in planning the procedure (step 51). If the predicted procedure results are acceptable (step 52), the proposed procedure may be planned or performed (step 54). If not, or if another, alternative, procedure is to be checked, an alternative procedure may be proposed (step 56) and the process repeated (steps 44 through 52) until a procedure is selected to be performed (step 54).

Figure 3:
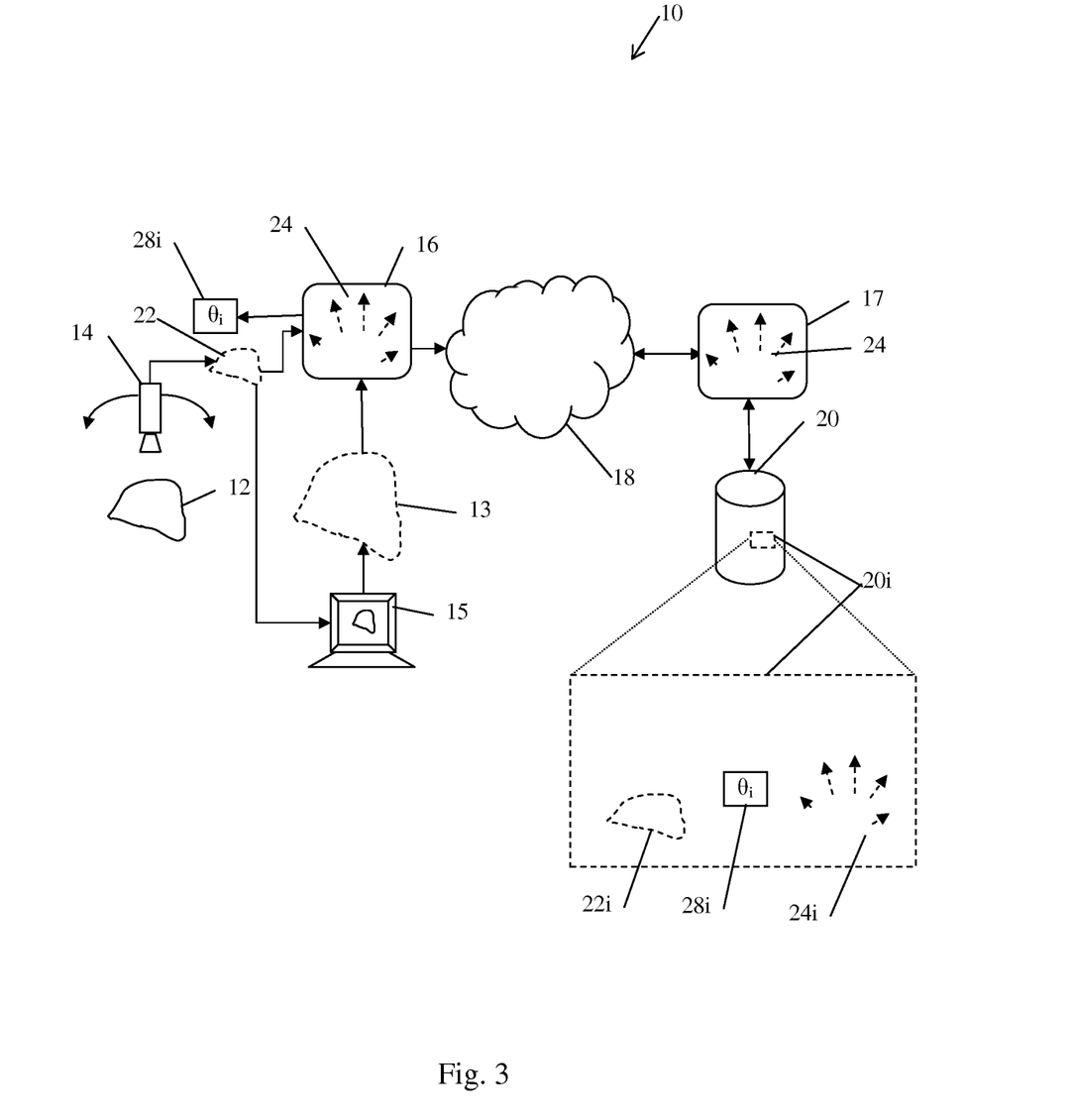
FIG. 3 schematically shows an alternative system for selecting a surgical procedure based on desired results, in accordance with some embodiments of the present invention.

In an inverse setup, a system in accordance with embodiments of the present invention may be used to select a directly based on desired results. FIG. 3 schematically shows an alternative system for selecting a surgical procedure based on desired results, in accordance with some embodiments of the present invention. As described above, at local station 16 creates surface representation 22 of scanned surface 12. Surface representation 22 may be input to user graphics station 15. A user at user graphics station 15 may manipulate surface representation 22, using standard image morphing techniques as are known in the art, to create a desired surface representation 13. Typically, desired surface representation 13 represents a desired surgery result. A processor associated with local station 16 may then calculate a deformation map 24. Deformation map 24 corresponds to a transformation of surface representation 22 to desired surface representation 13.

Deformation map 24 may be sent to server 17 via network 18, possibly together with surface representation 22. Server 17 may use deformation map 24 and surface representation 22 to query database 20 for a best matching record. For example, the query may entail searching database 20 for a record 20i with deformation map 24i that matches input deformation map 24. The query may in addition entail searching database 20 for a record 20i with a pre-surgery surface representation 22i that matches input pre-surgery surface representation 22. The retrieved record 20i includes surgical procedure parameters 28i. The retrieved procedure parameters 28i may then be returned via network 18 to local station 16. The retrieved procedure parameters 28i may then be used to plan a surgical procedure to modify scanned surface 12.

Figure 4:
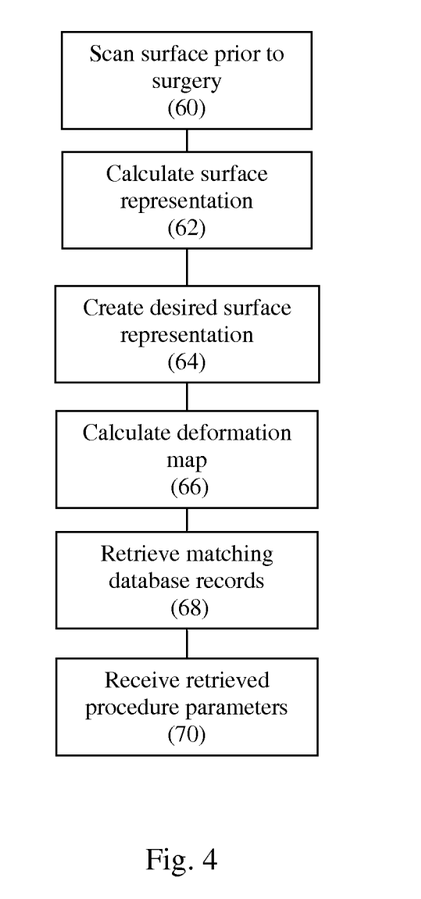
FIG. 4 is a flowchart of an alternative method for selecting a surgical procedure based on desired results, in accordance with some embodiments of the present invention.

FIG. 4 is a flowchart of an alternative method for selecting a surgical procedure based on desired results, in accordance with some embodiments of the present invention. As described above, a surface of a body part to be modified by surgery is scanned (step 60) and a representation of the surface is calculated (step 62). A user then uses a graphics interface to manipulate the surface representation to create a representation of the desired shape of the surface after modification by surgery (step 64). A processor is then operated to calculate a deformation map describing the transformation of the surface from the representation of the scanned surface to that of the desired surface (step 66). Alternatively, the distortion may have been created automatically during the manipulation of the surface representation. The deformation map may be used, possibly in association with other data, to query the database for matching records (step 68). The retrieved record includes parameters describing a surgical procedure. The retrieved surgical procedure parameters may then be sent to the user for consideration (step 70).

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claimed is:

1. A method for planning a current medical procedure to be performed on a body part of a current patient, the method comprising:

obtaining, using a computer, current first representation of a surface of the body part of the current patient;

retrieving, using the computer, at least one record from a database of records of previously performed medical procedures of previous patients, in which each record includes parameters of a previously performed procedure of said previously performed medical procedures, a first representation of the body part of the previous patient prior to performance of the previously performed procedure, and a second representation of a body part of the previous patient after the performance of the previously performed procedure, said at least one record being a best matching record to the current first representation of the current patient based on a similarity criterion between said current first representation of the first patient and said first representation of the body part of said previous patient;

creating a deformation map to characterize the transformation between the first and second representations of the body part of the previous patient, said map representing displacement between each of a plurality of points on the first representation of the previous patient and corresponding points on the second representation of the previous patient; and applying the deformation map to the first representation of the surface of the body part of the current patient to predict the transformation for the current patient.

2. A method as claimed in claim 1, wherein the step of obtaining a current first representation comprises scanning the body part.

3. A method as claimed in claim 1, wherein the similarity criterion refers to a similarity selected from a list of similarities consisting of:

similarity between the current second representation and the second representation of a record of the database of records;

similarity between the current first representation and the first representation of a record of the database of records; and similarity between a deformation map representing transformation of the current first representation into the current second representation and a deformation map representing transformation of the first representation into the second representation of a record of the database of records.

4. A method as claimed in claim 1, comprising billing a user per consultation.

5. A method for predicting a result of a current medical procedure to be performed on a body part of a current patient, the method comprising:

obtaining a current first representation of a surface of the body part of the current patient;

selecting parameters for the current medical procedure;

retrieving at least one record from a database of records of previously performed medical procedures of previous patients, in which each record includes parameters of a previously performed procedure of said previously performed medical procedures, a first representation of the body part of the previous patient prior to performance of the previously performed procedure, and a second representation of a body part of the previous patient after the performance of the previously performed procedure, said at least one record being a best matching record to the current first representation of the current patient based on a similarity criterion between said current first representation of the first patient and said first representation of the body part of said previous patient;

creating a deformation map to characterize the transformation between the first and second representations of the body part of the previous patient, said map representing displacement between each of a plurality of points on the first representation of the previous patient and corresponding points on the second representation of the previous patient; and applying the deformation map to the first representation of the surface of the body part of the current patient to predict the transformation for the current patient.

6. A method as claimed in claim 5, wherein the step of obtaining a current first representation comprises scanning the body part.

7. A method as claimed in claim 5, wherein the similarity criterion refers to a similarity selected from a list of similarities consisting of:

similarity between the selected parameters and the parameters of a record of the database of records; and similarity between the current first representation and the first representation of a record of the database of records.

8. A method as claimed in claim 5, comprising displaying the current second representation.

9. A method as claimed in claim 5, comprising billing a user per consultation.

10. A computer program product stored on a non-transitory tangible computer readable storage medium for planning a current medical procedure to be performed on a body part of a current patient, the computer program including code for:

obtaining a current first representation of a surface of the body part of the current patient; obtaining a current second representation of a desired result surface for the current medical procedure;

selecting parameters for the current medical procedure; retrieving at least one record from a database of records of previously performed medical procedures of previous patients, in which each record includes parameters of a previously performed procedure of said previously performed medical procedures, a first representation of the body part of the previous patient prior to performance of the previously performed procedure, and a second representation of a body part of the previous patient after the performance of the previously performed procedure, said at least one record being a best matching record to the current first representation of the current patient based on a similarity criterion between said current first representation of the first patient and said first representation of the body part of said previous patient;

creating a deformation map to characterize the transformation between the first and second representations of a body part of the previous patient, said map representing displacement between each of a plurality of points on the first representation of the previous patient and corresponding points on the second representation of the previous patient; and applying the deformation map to the first representation of the surface of the body part of the current patient to predict the transformation for the current patient.

11. A computer program product as claimed in claim 10, wherein the computer code for obtaining a current first representation comprises code for obtaining data from a scanner.

12. A computer program product as claimed in claim 10, wherein the computer code for generating a current second representation includes code for calculating a deformation map based on the first representation and the second representation of said at least one record and applying the deformation map to the current first representation.

13. A computer program product as claimed in claim 10, wherein the similarity criterion refers to a similarity selected from a list of similarities consisting of: similarity between the current second representation and the second representation of a record of the database of records; similarity between the current first representation and the first representation of a record of the database of records; similarity between a deformation map of a transformation of the current first representation into the current second representation and a deformation map of a transformation of the first representation into the second representation of a record of the database of records; and similarity between the selected parameters and the parameters of a record of the database of records.

* * * * *